(12) United States Patent
Maeda et al.

(10) Patent No.: US 8,013,193 B2
(45) Date of Patent: Sep. 6, 2011

(54) METHOD FOR PRODUCING ALCOHOL BY HYDROGENATING LACTONE AND CARBOXYLIC ACID ESTER IN LIQUID PHASE

(75) Inventors: Hirofumi Maeda, Takasago (JP); Kenji Inoue, Osaka (JP); Takaji Matsumoto, Kanagawa (JP); Izuru Nagasaki, Kanagawa (JP); Ryoji Noyori, Aichi (JP); Susumu Saito, Aichi (JP)

(73) Assignees: Kaneka Corporation, Osaka (JP); Takasago International Corporation, Tokyo (JP)

( * ) Notice: Subject to any disclaimer, the term of this patent is extended or adjusted under 35 U.S.C. 154(b) by 47 days.

(21) Appl. No.: 12/594,577

(22) PCT Filed: Apr. 2, 2008

(86) PCT No.: PCT/JP2008/000850
§ 371 (c)(1),
(2), (4) Date: Oct. 2, 2009

(87) PCT Pub. No.: WO2008/120475
PCT Pub. Date: Oct. 9, 2008

(65) Prior Publication Data
US 2010/0113842 A1    May 6, 2010

(30) Foreign Application Priority Data

Apr. 3, 2007   (JP) ................................. 2007-097618

(51) Int. Cl.
*C07C 29/149*   (2006.01)
(52) U.S. Cl. ........ 568/885; 568/814; 568/830; 568/864; 568/874
(58) Field of Classification Search .................... None
See application file for complete search history.

(56) References Cited

U.S. PATENT DOCUMENTS

| 4,885,411 | A | * | 12/1989 | De Thomas et al. | ........... 568/864 |
| 5,731,479 | A | * | 3/1998 | Antons | ........................ 568/864 |

FOREIGN PATENT DOCUMENTS

| JP | 63-185937 A | 8/1988 |
| JP | 2001-247499 A | 9/2001 |
| JP | 2004-300131 A | 10/2004 |
| JP | 2005-524704 | 8/2005 |
| WO | WO-2006/106483 A1 | 10/2006 |
| WO | WO-2007/017453 A1 | 2/2007 |
| WO | WO-2008/035123 A2 | 3/2008 |

OTHER PUBLICATIONS

H. Teunissen, et al., "Homogeneous Ruthenium Catalyzed Hydrogenation of Esters to Alcohols", Chem. Commun., pp. 1367-1368 (1998).
Internationall Search Report dated Jun. 30, 2008 (Form PCT/ISA/210).

* cited by examiner

*Primary Examiner* — Brian J Davis
(74) *Attorney, Agent, or Firm* — Peter F. Corless; Christine C. O'Day; Edwards Angell Palmer & Dodge LLP

(57) ABSTRACT

Disclosed is a method for producing an alcohol from a lactone or a carboxylic acid ester, which enables to produce an alcohol from a lactone or a carboxylic acid ester under relatively mild conditions with high yield and high catalytic efficiency. This method also enables to produce an optically active alcohol from an optically active lactone or an optically active carboxylic acid ester. Specifically disclosed is a method for producing an alcohol by hydrogen reducing a lactone or a carboxylic acid ester in the presence of a catalyst containing ruthenium and a phosphine compound represented by the following general formula (1):

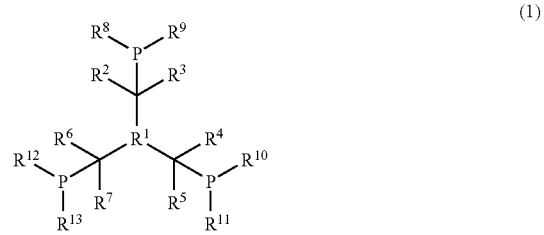

(1)

wherein $R^1$ represents a spacer; $R^2$, $R^3$, $R^4$, $R^5$, $R^6$ and $R^7$ independently represent a hydrogen atom, an alkyl group having 1-12 carbon atoms, an aryl group or a heterocyclic group; and $R^8$, $R^9$, $R^{10}$, $R^{11}$, $R^{12}$ and $R^{13}$ independently represent an alkyl group having 1-12 carbon atoms, an aryl group or a heterocyclic group.

10 Claims, No Drawings

METHOD FOR PRODUCING ALCOHOL BY HYDROGENATING LACTONE AND CARBOXYLIC ACID ESTER IN LIQUID PHASE

TECHNICAL FIELD

The present invention relates to a method for producing an alcohol by hydrogenating a lactone or a carboxylic acid ester.

BACKGROUND ART

There have been many reports on the method for producing an alcohol by hydrogenating a lactone or a carboxylic acid ester, with various catalysts and reaction modes. Patent Documents 1 to 3 and Non-Patent Document 1 describe hydrogenation reactions of lactones and carboxylic acid esters in fixed bed or liquid phase suspension systems. Patent Documents 4 to 6 and Non-Patent Documents 2 and 3 describe hydrogenation reactions of esters in the liquid phase, using ruthenium complexes that are formed from a ruthenium compound and an organic phosphine compound. Furthermore, methods for producing optically active alcohols by hydrogenating optically active carboxylic acids, are described in Patent Documents 7 and 8, and Non-patent Document 4.

Patent Document 1: JP-A No. 51-8203
Patent Document 2: DE3217429A1
Patent Document 3: JP-A No. 58-216131
Patent Document 4: JP-A No. 2001-247499
Patent Document 5: JP-A No. 2004-300131
Patent Document 6: JP-W No. 2005-524704
Patent Document 7: JP-W No. 2002-501817
Patent Document 8: JP-W No. 2002-501935
Patent Document 9: WO2006/106483
Patent Document 10: WO2006/106484
Non-Patent Document 1: Org. React., 1954, 8, 1
Non-Patent Document 2: J. Chem. Soc. Chem. Commun., 1980,
Non-Patent Document 3: Angew. Chem. Int. Ed., 2006, 45, 1113
Non-Patent Document 4: Adv. Synth. Cat., 2001, 343, 802

DISCLOSURE OF THE INVENTION

Problems to be Solved by the Invention

The methods described in the Patent Documents 1 to 3 and Non-Patent Document 1 all require hard reaction conditions such as high temperature or high pressure, and thus the methods are highly limited in the handling, production apparatuses, and the like. The hydrogenation reactions in the liquid phase as described in Patent Documents 4 to 6 and Non-Patent Documents 2 and 3 do not all satisfy both the yield and the catalytic efficiency, and cannot be said to be economically advantageous methods. Furthermore, the hydrogenation reactions for esters as described in Patent Document 5 and Non-Patent Document 2 involve the use of fluorine-containing alcohols as solvents, and thus have a problem to be addressed from the viewpoints of economic efficiency and environmental load. The method described in Non-Patent Document 3 employs 1,4-dioxane as a reaction solvent, which is economically disadvantageous and poses concerns for the influence on human body. Patent Documents 7 and 8 and Non-Patent Document 4 propose methods for producing alcohols by a hydrogenation reaction which is not accompanied by a decrease in the optical purity. Patent Documents 7 and 8 describe hydrogenation reactions of optically active malic acid in the presence of ruthenium oxide-rhenium-based catalysts, while Non-Patent Document 4 describes a hydrogenation reaction involving optically active α-hydroxy esters and α-amino esters using rhodium-platinum oxide catalysts. However, all these reactions require large amounts of catalyst for the raw materials, and thus pose a problem in terms of industrial production. Moreover, it is difficult to obtain 1,3-diols and 1,3-aminoalcohols with good yield from optically active β-hydroxy esters or optically active β-amino esters. The methods described in Patent Documents 9 and 10 make use of large excess of base, and therefore, it is difficult to hydrogenate optically active esters without lowering the optical purity.

Accordingly, it is an object of the present invention to provide a method for producing an alcohol from a lactone or a carboxylic acid ester, which is capable of producing an alcohol from a lactone or a carboxylic acid ester under relatively mild conditions with high yield and high catalytic efficiency, and is capable of producing an optically active alcohol from an optically active lactone and an optically active carboxylic acid ester.

It is another object of the present invention to provide a method for producing an alcohol from a lactone or a carboxylic acid ester, which includes the advantageous features described above and has the environmental load reduced to the minimum.

Means for Solving the Problems

Under such circumstances, the inventors of the present invention devotedly conducted investigations, and as a result, they found that when a specific ruthenium catalyst formed from a ruthenium compound and a phosphine compound is used, and an alcohol-based solvent is employed as a reaction solvent, an alcohol is produced from a lactone or a carboxylic acid ester with high yield and high catalytic efficiency under relatively mild conditions, and an optically active alcohol is produced with high yield from an optically active lactone and an optically active carboxylic acid ester, thus completing the present invention.

Specifically, the present invention relates to the following [1] to [10].

[1] A method for producing an alcohol, including subjecting a lactone or a carboxylic acid ester to hydrogen reduction in a solvent or without solvent, in the presence of a catalyst containing ruthenium and a phosphine compound represented by the following formula (1):

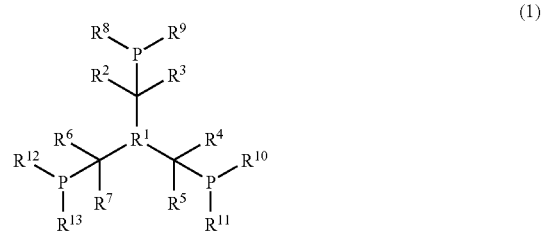

wherein $R^1$ represents a spacer; $R^2$, $R^3$, $R^4$, $R^5$, $R^6$ and $R^7$ each independently represent a hydrogen atom, or an alkyl group having 1 to 12 carbon atoms, an aryl group or a heterocyclic group; and $R^8$, $R^9$, $R^{10}$, $R^{11}$, $R^{12}$ and $R^{13}$ each independently represent an alkyl group having 1 to 12 carbon atoms, an aryl group or a heterocyclic group.

[2] The method for production according to [1], wherein the lactone or carboxylic acid ester that is subjected to reduction is an optically active form, and the optical purity of the alcohol produced by the reduction retains an optical purity value of 90% or more of the value of the substrate that is subjected to reduction.

[3] The method for production according to [1] or [2], wherein the catalyst containing ruthenium and a phosphine compound is produced for immediate use.

[4] The method for production according to any one of [1] to [3], wherein the catalyst containing ruthenium and a phosphine compound is a complex represented by the following formula (2):

$$[Ru_2(\mu-X^1)_3(Phos)_2]X^2 \quad (2)$$

wherein $X^1$ represents a halogen atom; $X^2$ represents a counter anion; and Phos represents the phosphine compound represented by the formula (1) above.

[5] The method for production according to any one of [1] to [3], wherein the catalyst containing ruthenium and a phosphine compound is a complex represented by the following formula (3):

$$[Ru(Phos)(L^1)(L^2)(L^3)](X^3)_2 \quad (3)$$

wherein $L^1$, $L^2$ and $L^3$, which may be present singly or linked together, each represent a neutral ligand or a coordinating solvent; $X^3$ represents a counter anion; and Phos represents the phosphine compound represented by the formula (1) above.

[6] The method for production according to any one of [1] to [3], wherein the catalyst containing ruthenium and a phosphine compound is a complex represented by the following formula (4):

$$[RuH(BH_4)(Phos)] \quad (4)$$

wherein Phos represents the phosphine compound represented by the formula (1) above.

[7] The method for production according to any one of [1] to [3], wherein the catalyst containing ruthenium and a phosphine compound is a complex represented by the following formula (5):

$$[Ru(H)(OAC)(Phos)] \quad (5)$$

wherein Ac represents an acetyl group; and Phos represents the phosphine compound represented by the formula (1) above.

[8] The method for production according to any one of [1] to [7], wherein the solvent used in the hydrogenation reaction is an alcohol solvent.

[9] The method for production according to any one of [1] to [8], wherein an additive is added to the reaction system.

[10] The method for production according to any one of [1] to [9], wherein a reducing agent is added to the reaction system as a co-catalyst.

Effects of the Invention

According to the method for production of the present invention, an alcohol can be produced with high yield and high catalytic efficiency by hydrogenating a lactone and a carboxylic acid ester in the liquid phase. The method of the present invention is carried out under relatively low pressure and low temperature conditions, and thus is an industrially useful production method. Furthermore, an optically active alcohol can be produced from an optically active lactone and an optically active carboxylic acid ester with high yield.

BEST MODE FOR CARRYING OUT THE INVENTION

Hereinafter, the present invention will be described in detail.

As the carboxylic acid ester that is used as a raw material in the present invention, an aliphatic carboxylic acid ester, an aromatic carboxylic acid ester or the like may be mentioned. This ester may be an ester derived from a monocarboxylic acid or may be an ester derived from a polycarboxylic acid.

As the ester that is used in the present invention, there may be mentioned an alkyl ester such as methyl ester, ethyl ester, propyl ester, butyl ester, hexyl ester, or octyl ester; an aryl ester such as phenyl ester, biphenyl ester or naphthyl ester; an aralkyl ester such as benzyl ester or 1-phenethyl ester; or the like, of a carboxylic acid that will be described below.

The aliphatic carboxylic acid may be a mono- or polycarboxylic acid having 2 to 30 carbon atoms, and specific examples thereof include acetic acid, propionic acid, butyric acid, valeric acid, hexanoic acid, heptanoic acid, octanoic acid, nonanoic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, and the like.

These aliphatic carboxylic acids may be substituted with a substituent. Examples of the substituent include an alkyl group, an alkoxy group, a halogen atom, an amino group, an aryl group, a heteroaryl group, an aralkyl group, a silyloxy group, a hydroxyl group, and the like.

The alkyl group may be linear, branched or cyclic. Examples thereof include a methyl group, an ethyl group, an n-propyl group, an isopropyl group, an n-butyl group, an isobutyl group, an s-butyl group, a t-butyl group, an n-pentyl group, an n-hexyl group, an n-octyl group, a cyclopropyl group, a cyclopentyl group, a cyclohexyl group, and the like.

The alkoxy group may be linear, branched or cyclic. Examples thereof include a methoxy group, an ethoxy group, an n-propoxy group, an isopropoxy group, an n-butoxy group, an isobutoxy group, an s-butoxy group, a t-butoxy group, an n-pentyloxy group, an n-hexyloxy group, an n-octyloxy group, a cyclopentyloxy group, a cyclohexyloxy group, and the like.

As the halogen atom, a fluorine atom, a chlorine atom, a bromine atom, and an iodine atom may be mentioned.

Examples of the amino group include an amino group; a mono- or dialkylamino group such as an N-methylamino group, an N,N-dimethylamino group, an N,N-diethylamino group, an N,N-diisopropylamino group, or an N-cyclohexylamino group; a mono- or diarylamino group such as an N-phenylamino group, an N,N-diphenylamino group, an N-naphthylamino group, or an N-naphthyl-N-phenylamino group; a mono- or diaralkylamino group such as an N-benzylamino group or an N,N-dibenzylamino group; an acylamino group such as a formylamino group, an acetylamino group, a propionylamino group, a pivaloylamino group, a pentanoylamino group, a hexanoylamino group, or a benzoylamino group; an alkoxycarbonylamino group such as a methoxycarbonylamino group, an ethoxycarbonylamino group, an n-propoxycarbonylamino group, an n-butoxycarbonylamino group, a tert-butoxycarbonylamino group, a pentyloxycarbonylamino group, or a hexyloxycarbonylamino group; an aryloxycarbonylamino group such as a phenyloxycarbonylamino group; an aralkyloxycarbonylamino group such as a benzyloxycarbonylamino group; a sulfonylamino group such as a benzenesulfonylamino group, a 4-nitrobenzenesulfonylamino group, a 2-nitrobenzenesulfonylamino group, or a p-toluenesulfonylamino group; and the like.

The aryl group may be a phenyl group, a naphthyl group, a biphenyl group or the like, and these aryl groups may be substituted with such an alkyl group, alkoxy group, halogen atom, amino group or the like as mentioned above.

The heteroaryl group may be a 5- to 8-membered, preferably 5- or 6-membered, monocyclic heteroaryl group or polycyclic or fused ring type heteroaryl group, each containing, for example, 2 to 15 carbon atoms and at least one, preferably 1 to 3, heteroatoms such as a nitrogen atom, an oxygen atom and a sulfur atom. Specific examples thereof include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzimidazolyl group, a benzoxazolyl group, a benzothiazolyl group and the like.

The aralkyl group may be a benzyl group, a 1-phenethyl group or the like.

The silyloxy group may be, for example, a trimethylsilyloxy group, a t-butyldimethylsilyloxy group, a t-butyldiphenylsilyloxy group.

Examples of the aromatic carboxylic acid include benzoic acid, naphthalenecarboxylic acid, pyridinecarboxylic acid, quinolinecarboxylic acid, furancarboxylic acid, thiophenecarboxylic acid, or the like.

These aromatic carboxylic acids may be substituted with such an alkyl group, alkoxy group, halogen atom, amino group, aryl group, heteroaryl group, aralkyl group, hydroxyl group or the like as mentioned above.

As the lactone that is used in the present invention, β-lactone, γ-lactone, δ-lactone and the like may be mentioned, and these lactones may be substituted with such an alkyl group, alkoxy group, halogen atom, amino group, aryl group, heteroaryl group, aralkyl group, hydroxyl group or the like as mentioned above.

Next, the catalyst that is used in the present invention will be described.

As the ruthenium constituting a component of the catalyst used in the present invention, for example, a ruthenium compound may be mentioned, and specific examples of the ruthenium compound include $RuCl_2(DMSO)_4$, $RuCl_3 \cdot nH_2O$, $(cod)_2Ru(\mu\text{-OAc})$, $(cod)_2Ru(\mu\text{-}O_2CCF_3)$, $(cod)Ru(\eta^2\text{-}O_2CCF_3)_2$, $(cod)Ru(\eta^3\text{-methallyl})_2$, $Ru_2(CO)_6(C_8H_8)$, $RuCl(CO)_3$ $(C_3H_5)$, $Ru(C_5H_5)_2$, $Ru(C_5H_5)(CH_3COC_5H_4)$, $Ru(C_5H_5)(C_5H_4CH_3)$, $[Ru(cod)Cl_2]n$, $[Ru(benzene)Cl_2]_2$, $[Ru(benzene)Br_2]_2$, $[Ru(benzene)I_2]_2$, $[Ru(p\text{-cymene})Cl_2]_2$, $[Ru(p\text{-cymene})Br_2]_2$, $[Ru(p\text{-cymene})I_2]_2$, $[Ru(mesitylene)Cl_2]_2$, $[Ru(mesitylene)Br_2]_2$, $[Ru(mesitylene)I_2]_2$, $RuCl_2(PPh_3)_3$, $RuBr_2(PPh_3)_3$, $RuI_2(PP_3)_3$, $RuHCl(PPh_3)_3(CO)$, $RuH_2(PPh_3)_4$, $RuH_4(PP^3)_3$, $RuClH(PPh_3)_3$ and the like. In the examples mentioned above, DMSO represents dimethylsulfoxide, and cod represents 1,5-cyclooctadiene.

Next, the phosphine compound that is used in the present invention will be described.

The phosphine compound that is used in the present invention is a phosphine compound represented by the following formula (1), and is a phosphine compound having tridentate coordination capacity (tridentate phosphine).

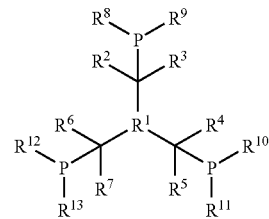

(1)

wherein $R^1$ represents a spacer; $R^2, R^3, R^4, R^5, R^6$ and $R^7$ each independently represent a hydrogen atom, or an alkyl group having 1 to 12 carbon atoms, an aryl group or a heterocyclic group; and $R^8, R^9, R^{10}, R^{11}, R^{12}$ and $R^{13}$ each independently represent an alkyl group having 1 to 12 carbon atoms, an aryl group or a heterocyclic group.

As the alkyl group represented by $R^2$ to $R^{13}$ in the phosphine compound represented by the formula (1), there may be mentioned an alkyl group having, for example, 1 to 15 carbon atoms, preferably 1 to 12 carbon atoms, more preferably 1 to 10 carbon atoms, and even more preferably 1 to 6 carbon atoms, which may be linear, branched or cyclic. Specific examples thereof include a methyl group, an ethyl group, an n-propyl group, an isopropyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentane-3-yl group, a cyclopropyl group, a cyclobutyl group, a cyclopentyl group, a cyclohexyl group, a methylcyclopentyl group, a methylcyclohexyl group and the like.

The aryl group represented by $R^2$ to $R^{13}$ in the phosphine compound represented by the formula (1) may be, for example, an aryl group having 6 to 14 carbon atoms, and specific examples thereof include a phenyl group, a naphthyl group, an anthryl group, a phenanthryl group, a biphenyl group, and the like. These aryl groups may be substituted with a substituent, and the substituent may be an alkyl group, an alkoxy group, an aryl group, a heterocyclic group or the like. Specific examples of the substituent may include such as those mentioned above.

As the heterocyclic group in the phosphine compound represented by the formula (1), an aliphatic or aromatic heterocyclic group may be mentioned, and the heterocyclic group may be a 5- to 8-membered, preferably 5- to 6-membered, monocyclic, polycyclic or fused ring type heterocyclic group containing 2 to 14 carbon atoms, and at least one heteroatom such as a nitrogen atom, an oxygen atom or a sulfur atom as a heteroatom. Specific examples of the aliphatic heterocyclic group include, for example, 2-oxopyrrolidyl group, a piperidino group, a piperazinyl group, a morpholino group, a tetrahydrofuryl group, a tetrahydropyranyl group, a tetrahydrothienyl group, and the like. Specific examples of the aromatic heterocyclic group include, for example, a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzimidazolyl group, a benzoxazolyl group, a benzothiazolyl group, and the like.

As the spacer represented by $R^1$ in the phosphine compound represented by the formula (1), an alkanetriyl group, a cycloalkanetriyl group, an arenetriyl group, a heteroatom-containing group or the like may be mentioned. The alkanetriyl group may be, for example, such a group having 1 to 4 carbon atoms, and specific examples include a methanetriyl group, a 1,1,1-ethanetriyl group, a 1,1,2-ethanetriyl group, a 1,1,1-propanetriyl group, a 1,1,2-propanetriyl group, a 1,2,3-propanetriyl group, and the like. The cycloalkanetriyl group may be, for example, such a group having 5 to 7 carbon atoms, and specific examples include a 1,1,2-cyclopentanetriyl group, a 1,2,3-cyclopentanetriyl group, a 1,1,2-cyclohexanetriyl group, a 1,3,5-cyclohexanetriyl group, a 1,3,5-cycloheptanetriyl group, and the like. The arenetriyl group may be, for example, such a group having 6 to 20 carbon atoms, and specific examples include a 1,3,5-benzenetriyl group, a 1,3,4-benzenetriyl group, a 1,2,3-benzenetriyl group, and the like. The heteroatom-containing group may be boron (B), silicon (RSi), tin (RSn), or phosphorus (P). The group R in RSi and RSn may be, for example, an alkyl group having 1 to 12 carbon atoms, an aryl group having 6 to 12 carbon atoms, or the like. Specific examples of the phosphine compound represented by the formula (1) include 1,1,1-tris(dimethylphosphinomethyl)ethane, 1,1,1-tris{bis(4-methoxyphenyl)phosphinomethyl}ethane, 1,1,1-tris{bis(4-methylphenyl)phosphinomethyl}ethane, 1,1,1-tris(diethylphosphinomethyl)ethane, 1,1,1-tris(dicyclohexylphosphinomethyl)ethane, 1,1,1-tris(diphenylphosphinomethyl)ethane, 1,1,1-tris(diphenylphosphinomethyl)methane, 1,1,1-tris(diphenylphosphinomethyl)propane, 1,1,1-tris(diphenylphosphinomethyl)-2-methylpropane, 1,1,1-tris(diphenylphosphinomethyl)butane, 1,1,1-tris(diphenylphosphinomethyl)-2,2-dimethylpropane, 1,3,5-tris(diphenylphosphinomethyl)cyclohexane, and the like, and preferred examples include 1,1,1-tris(diphenylphosphinomethyl)ethane, 1,1,1-tris{bis(4-methoxyphenyl)phosphinomethyl}ethane, 1,1,1-tris{bis(4-methylphenyl)phosphinomethyl}ethane, 1,1,1-tris(diphenylphosphinomethyl)-2,2-dimethylpropane, 1,1,1-tris(diphenylphosphinomethyl)methane, and the like. These phosphine compounds may be directly used in the reaction, or may be first derived into stable phosphine-borane compounds and then used.

As the catalyst containing ruthenium and the phosphine compound represented by the formula (1) that can be used in the present invention, a complex represented by the following formula (2) may be mentioned.

wherein $X^1$ represents a halogen atom; $X^2$ represents a counter anion; and Phos represents the phosphine compound represented by the formula (1).

Specific examples of the counter anion ($X^2$ in the formula) of the complex represented by the formula (2) include Cl, Br, I, $I_3$, $ClO_4$, $PF_6$, $BPh_4$, $B(C_6F_5)_4$, $BF_4$, $CF_3SO_3$, and the like, and preferred examples are Cl and $BPh_4$.

The complex (2) may be used after the complex is separately prepared and then isolated, or may be prepared in situ in the system for immediate use and then directly used. The complex can be obtained by, for example, a method described in the literature (Venanzi, et al., Inorg. Chem., 1988, 27, 604-610). That is, $RuCl_2(DMSO)_4$ is reacted with, for example, tris-1,1,1-(diphenylphosphinomethyl)ethane (hereinafter, referred to as triphos) as the phosphine compound, and thereby $[Ru_2(\mu-Cl)_3(triphos)_2]Cl$ is obtained. Furthermore, the complex can also be obtained by subjecting $[Ru(benzene)Cl_2]_2$, instead of $RuCl_2(DMSO)_4$, to the action of triphos.

The counter anion moiety ($X^2$ in the formula (2)) of the complex (2) obtained as described above, can be exchanged with a corresponding counter anion by reacting the complex with an inorganic salt such as $NaClO_4$, $NaPF_6$, $NaBPh_4$, $NaB(C_6F_5)_4$, $NaBF_4$ or NaOTf.

As the catalyst containing ruthenium and the phosphine compound represented by the formula (1) that can be used in the present invention, a complex represented by the following formula (3) may be mentioned.

wherein $L^1$, $L^2$ and $L^3$, which may be present singly or linked together, each represent a ligand or a coordinating solvent; $X^3$ represents a counter anion; and Phos represents the phosphine compound represented by the formula (1) above.

The ligand ($L^1$, $L^2$ and $L^3$ in the formula (3)) of the complex represented by the formula (3) may be a phosphine compound, an amine compound or the like, and preferred examples include triphenylphosphine, 2-mercaptopyridine, 2-pyridinone, 2-aminomethylpyridine and the like.

Examples of the coordinating solvent ($L^1$, $L^2$ and $L^3$ in the formula (3)) of the complex represented by the formula (3) include alcohols, ethers, water, sulfoxides and amides, and preferably, acetonitrile, dimethylsulfoxide, N,N-dimethylformamide and the like.

Specific examples of the counter anion ($X^3$ in the formula (3)) of the complex represented by the formula (3) include $ClO_4$, $PF_6$, $BPh_4$, $B(C_6F_5)_4$, $BF_4$, $CF_3SO_3$, and the like, and preferably $BF_4$ and $CF_3SO_3$.

The complex (3) may be used after the complex is separately prepared and then isolated, or may be prepared in situ in the system for immediate use and then directly used. The complex can be obtained by, for example, a method described in the literature (Venanzi, et al., Inorg. Chem., 1988, 27, 604-610). That is, for example, $[Ru_2(\mu-Cl)_3(triphos)_2]Cl$ mentioned above and 4 equivalents of silver trifluoromethanesulfonate are heated under stirring in an acetonitrile solvent, and thereby $[Ru(triphos)(MeCN)_3](CF_3SO_3)_2$ is obtained.

As the catalyst containing ruthenium and the phosphine compound represented by the formula (1) that can be used in the present invention, a complex represented by the following formula (4) may be mentioned.

wherein Phos represents the phosphine compound represented by the formula (1).

The complex represented by the formula (4) may be used after the complex is separately prepared and then isolated, or may be prepared in situ in the system for immediate use and then directly used. The complex can be obtained by, for example, a method described in the literature (Venanzi, et al., Inorg. Chem., 1987, 26, 2692-2695). That is, $[RuH(BH_4)(triphos)]$ is obtained by, for example, stirring $[Ru(triphos)(NCMe)_3](CF_3SO_3)_2$ mentioned above and an excess amount of sodium borohydride in a methanol solvent.

As another catalyst containing ruthenium and the phosphine compound represented by the formula (1) that can be used in the present invention, a complex represented by the following formula (5) may be mentioned.

wherein Ac represents an acetyl group; and Phos represents the phosphine compound represented by the formula (1).

The complex represented by the formula (5) may be used after the complex is separately prepared and then isolated, or may be prepared in situ in the system for immediate use and then directly used. The complex can be obtained by, for example, a method described in the literature (Dyson, et al., Inorg. Chem., 2008, 47, 381-390). That is, for example, [Ru(H)(OAc)(triphos)] is obtained by stirring [Ru(H)(OAc)(PPh$_3$)$_3$] and a tridentate phosphine compound (triphos) in a toluene solvent.

The amount of use of the complex may vary depending on the substrate of hydrogenation, the reaction conditions, the type of catalyst or the like, but the amount of use is typically, in terms of the molar ratio of ruthenium metal relative to the substrate of hydrogenation, in the range of 0.001% by mole to 1.0% by mole, and preferably 0.01% by mole to 0.25% by mole.

The method for production of the present invention can be suitably carried out without solvent or in a solvent, but it is preferable to use a solvent. As the solvent that may be used, a solvent capable of dissolving the substrate and the complex is preferred, and a single solvent or a mixed solvent is used. Specific examples include aromatic hydrocarbons such as toluene and xylene; aliphatic hydrocarbons such as hexane and heptane; halogenated hydrocarbons such as methylene chloride and chlorobenzene; ethers such as diethyl ether, tetrahydrofuran and 1,4-dioxane; alcohols such as methanol, ethanol, isopropanol, n-butanol and 2-butanol; polyols such as ethylene glycol, propylene glycol, 1,2-propanediol and glycerin; esters such as methyl acetate, ethyl acetate and butyl acetate; nitriles such as acetonitrile; amides such as N,N-dimethylformamide and N-methylpyrrolidone; amines such as pyridine and triethylamine; and the like. Among these, single or mixed solvents containing at least one or more alcohols, in other words, alcohol solvents are preferable. Particularly preferred are methanol, n-butanol and isopropanol. The amount of use of the solvent can be appropriately selected in accordance with the reaction conditions or the like, but the amount of use may be 0.01 mol/L to 1000 mol/L, and preferably 1.0 mol/L to 10.0 mol/L, based on the raw materials.

According to a suitable exemplary embodiment of the method for production of the present invention, the method can be carried out by adding an additive to the reaction system, and thereby hydrogen reduction proceeds smoothly. Examples of the additive can include a base, an acid and/or a reducing agent, and preferably a base and/or a reducing agent.

According to the suitable exemplary embodiment of the method for production of present invention, the base that may be used to be added to the reaction system, may be an organic base compound or an inorganic base compound.

Specific examples of the organic base compound that is used in the present invention include amines such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0]undec-7-ene, tri-n-butylamine and N-methylmorpholine. Particularly preferred compounds among these are triethylamine, ethyldiisopropylamine and the like.

Examples of the inorganic base compound include alkali metal compounds such as carbonates of alkali metals, hydroxides of alkali metals, alkali metal alkoxides, and alkali metal borates.

Specific examples of the inorganic base compound that is used in the present invention include alkali metal carbonates such as potassium carbonate, sodium carbonate, lithium carbonate and cesium carbonate; alkali metal hydroxides such as sodium hydroxide, potassium hydroxide and lithium hydroxide; alkali metal alkoxides such as sodium methoxide, sodium t-butoxide, potassium methoxide, potassium t-butoxide, lithium methoxide, and lithium t-butoxide; alkali metal borates such as sodium tetraphenylborate, and lithium tetraphenylborate; and the like. Particularly preferred compounds among these are sodium methoxide, sodium t-butoxide, lithium methoxide, lithium t-butoxide, and the like.

The amount of use of the base compound that is used in the present invention can be appropriately selected in accordance with the ruthenium complex used, reaction conditions or the like, but the amount of use is typically 0.1 equivalents to 1000 equivalents, and preferably 1 equivalent to 100 equivalents, based on the ruthenium complex.

The base compound may be directly added to the reaction system, or may also be added to the reaction system in the form of a solution prepared by dissolving the base compound in a reaction solvent or the like beforehand.

According to the suitable exemplary embodiment of the method for production of the present invention, the acid that may be used to be added to the reaction system, may be an inorganic acid or an organic acid.

Specific examples of the inorganic acid include hydrochloric acid, hydrobromic acid, sulfuric acid, phosphoric acid and the like. Specific examples of the organic acid include formic acid, acetic acid, trichloroacetic acid, trifluoroacetic acid, methanesulfonic acid, benzenesulfonic acid, p-toluenesulfonic acid, trifluoromethanesulfonic acid, and the like.

The amount of use of the acid compound that is used in the present invention can be appropriately selected in accordance with the ruthenium complex used, reaction conditions or the like, but the amount of use is typically 0.1 equivalents to 1000 equivalents, and preferably 1 equivalent to 100 equivalents.

The acid compound may be directly added to the reaction system, or may also be added to the reaction system in the form of a solution prepared by dissolving the acid compound in a reaction solvent or the like beforehand.

As the reducing agent that can be used in the present invention, Zn, Zn(BH$_4$)$_2$, LiAlH$_4$, LiAlH(OBu-t)$_3$, NaAlH$_4$, LiAlHEt$_3$, LiHB(Et)$_3$ and the like may be mentioned.

According to the present invention, the reaction temperature employed at the time of performing hydrogen reduction is 30° C. to 150° C., and preferably 40° C. to 120° C. If the reaction temperature is too low, large amounts of unreacted raw materials may remain behind, and if the reaction temperature is too high, decomposition of the raw materials, the catalyst or the like may occur, which is not preferable.

According to the present invention, the pressure of hydrogen employed at the time of performing hydrogen reaction is 0.1 MPa to 5.0 MPa, preferably 1.0 MPa to 5.0 MPa, and more preferably 1.0 MPa to 4.0 MPa.

In regard to the reaction time, a sufficiently high raw material conversion rate can be obtained with about 3 hours to 20 hours.

After completion of the reaction, the desired alcohols can be obtained by adopting conventionally used purification methods such as extraction, filtration, crystallization, distillation and various chromatographic methods, either singly or in appropriate combinations.

EXAMPLES

Hereinafter, the present invention will be described in detail by way of Examples, but the present invention is not at all intended to be limited by these Examples. The apparatuses used in the measurement of properties in the various Examples are as follows.

NMR: NMR A-400 manufactured by JEOL, Ltd.

Gas chromatography: 5890-11 manufactured by Shimadzu Corp.

ZB-WAX (Phenomenex) 30 m (length)×0.25 mm (I.D.), 0.25 μm (thickness)

High performance liquid chromatography: JASCO GULLIVER SERIES manufactured by JASCO Corp.

Inertsil ODS-3V (GL Science) 25 μm×4.6×250 mm

In addition, triphos[1,1,1-tris(diphenylphosphinomethyl)ethane], triphos-Tol[1,1,1-tris{bis(4-methylphenyl)phosphinomethyl}ethane], triphos-An[1,1,1-tris{bis(4-methoxyphenyl)phosphinomethyl}ethane], tBu-triphos[1,1,1-tris(diphenylphosphinomethyl)-2,2-dimethylpropane], and H-triphos[1,1,1-tris(diphenylphosphinomethyl)methane] in the Examples are as follows. The triphos-Tol (Journal of Organometallic Chemistry, 1994, 468(1-2), 149-163), tBu-triphos (Tetrahedron, 2007, 63, 4450-4458), and H-triphos (Chem. Ber., 1994, 127, 501-506) were synthesized according to the methods described in the literature.

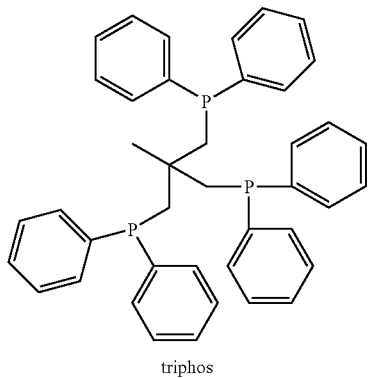

triphos

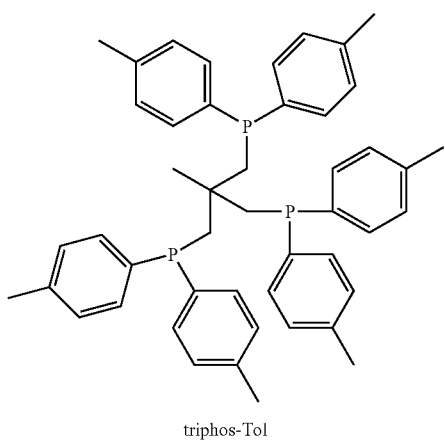

triphos-Tol

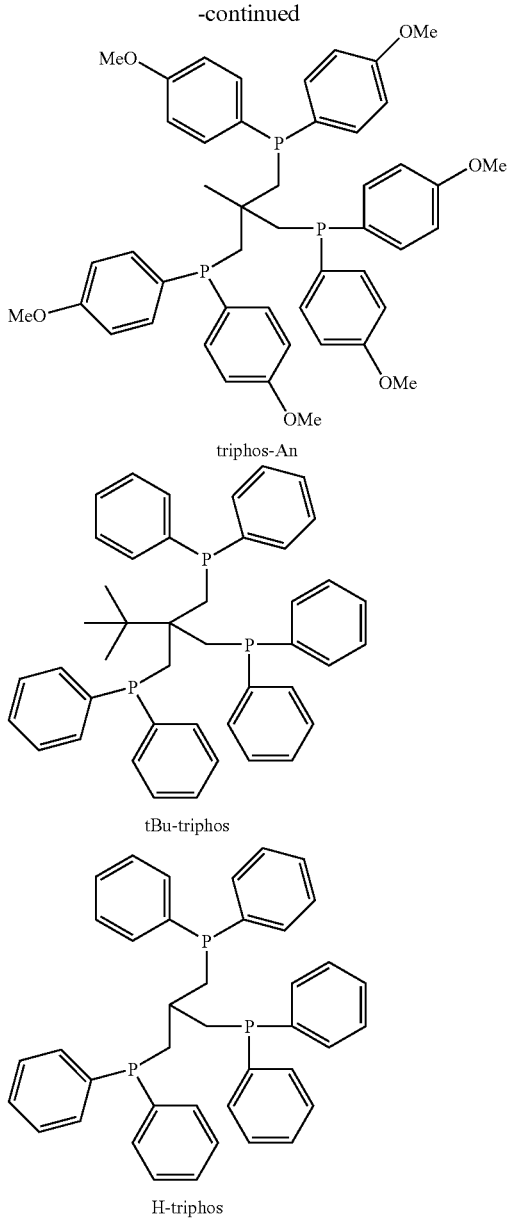

triphos-An tBu-triphos

H-triphos

Synthesis of triphos-An.3BH$_3$[1,1,1-tris{bis(4-methoxyphenyl)phosphinomethyl}ethane.3BH$_3$]

Under a nitrogen atmosphere, potassium tert-butoxide (1.98 g) and dimethylsulfoxide (22 ml) were added into a 200-ml three-necked flask, and the mixture was stirred at room temperature. HP(4-MeO—C$_6$H$_4$)$_2$ (4.34 g) dissolved in dimethylsulfoxide (7 ml) was added thereto dropwise, and the resulting mixture was stirred for one hour. Subsequently, 1,3-dichloro-2-(chloromethyl)-2-methylpropane (manufactured by Sigma Aldrich Company) (773 mg) was added thereto dropwise, and the resulting mixture was stirred at a bath temperature of 130° C. for 2 hours. After adding diethyl ether (55 ml), the mixture was ice-cooled, and degassed distilled water (55 ml) was added to the mixture. The mixture was partitioned into an aqueous phase and an organic phase, and then the aqueous phase was extracted three times with 44 ml of diethyl ether. The organic phase and the diethyl ether extracts were combined, and the combined liquid was washed with degassed distilled water and saturated brine, and was dried over anhydrous sodium sulfate. The dried product was filtered through a glass filter under a nitrogen atmosphere, and the organic solvent was removed under reduced pressure. Tetrahydrofuran (17.6 ml) was added to the residue, and a $BH_3$.tetrahydrofuran solution (19.7 ml) was added thereto dropwise under ice cooling. The mixture was stirred for one hour. The reaction liquid was poured into an aqueous solution of hydrochloric acid, subsequently ethyl acetate (20 ml) was added thereto, and the resulting mixture was stirred. The mixture was partitioned into an aqueous phase and an organic phase, and then the aqueous phase was extracted two times with 20 ml of ethyl acetate. The organic phase and the ethyl acetate extracts were combined, and the combined liquid was washed with water and with saturated brine, and dried over anhydrous sodium sulfate. The dried product was filtered, the organic solvent was removed under reduced pressure, and then the residue was purified by silica gel chromatography.

1,1,1-tris{bis(4-methoxyphenyl)phosphinomethyl}ethane.$3BH_3$ 1.70 g (yield 45.5%)

$^1$H NMR ($CDCl_3$): 7.55 dd (12H), 6.91 d (12H), 3.81 (18H), 2.77 d (6H), 1.55 br (9H), 0.77 s (3H)

$^{31}$P[$^1$H] NMR ($CD_2Cl_2$) external reference $H_3PO_4$:5.74 s

[$RU_2$ ($\mu$-Cl)$_3$ (triphos)$_2$]Cl, [Ru($CH_3CN$)$_3$(triphos)] ($CF_3SO_3$)$_2$ (Inorganic Chemistry, 1988, 27, 604-610), [Ru(H)($BH_4$)(triphos)] (Inorganic Chemistry, 1987, 26, 2692-2695), and [Ru(H)(OAc)(triphos)] (Inorganic Chemistry, 2008, 47, 381-390) were synthesized according to previously reported documents.

Synthesis of [$Ru_2(\mu\text{-Cl})_3$(triphos)$_2$]Cl

Under an argon atmosphere, triphos (1.22 g) dissolved by heating in 10 ml of toluene, was added dropwise to a suspension of [$RuCl_2(DMSO)_4$] (960 mg) in 40 ml of toluene at room temperature. The mixture was heated and stirred at 80° C. for one hour, and at 90° C. for 14 hours. The reaction liquid was left to cool to room temperature, and then precipitated crystals were collected by suction filtration under an argon atmosphere, and were washed with 10 ml of toluene and 10 ml of diethyl ether.

[$Ru_2(\mu\text{-Cl})_3$(triphos)$_2$]Cl 1.24 g (yield 80%)

$^1$H NMR ($CDCl_3$):7.40 br t (24H), 7.18 t (12H), 6.85 (2H), 2.24 br s (12H), 1.58 br q (6H)

$^{31}$P[$^1$H] NMR ($CDCl_3$) external reference $H_3PO_4$:36.00 s

Synthesis of [Ru($CH_3CN$)$_3$(triphos)]($CF_3SO_3$)$_2$

Under an argon atmosphere, Ag($CF_3SO_3$) (280 mg) was added to a solution of [$Ru_2(\mu\text{-Cl})_3$(triphos)$_2$]Cl (420 mg) in 20 ml of acetonitrile at room temperature, and the resulting reaction suspension was heated and stirred under reflux for 6 hours. The reaction liquid was left to cool to room temperature, subsequently a salt precipitated therefrom was filtered through Celite under an argon atmosphere, and the filtrate was concentrated to solid dryness. 5 ml of acetonitrile and 30 ml of toluene were added thereto, and the mixture was filtered through Celite under an argon atmosphere to remove any insoluble matters. While the filtrate was stirred at room temperature, 10 ml of diethyl ether was added dropwise to the filtrate, and the mixture was further stirred for 14 hours. Precipitated crystals were collected by suction filtration under an argon atmosphere, and were washed with 5 ml of toluene and 10 ml of diethyl ether.

[Ru($CH_3CN$)$_3$(triphos)]($CF_3SO_3$)$_2$ 280 mg (yield 92%)

$^1$H NMR ($CD_2Cl_2$):7.30 m (30H), 2.52 br s (3H), 2.34 s (9H), 1.71 br q (3H)

$^{31}$P[$^1$H] NMR ($CD_2Cl_2$) external reference $H_3PO_4$:26.60 s

Synthesis of [Ru(H)($BH_4$)(triphos)]

Under an argon atmosphere, $NaBH_4$ (220 mg) was slowly added to a solution of [Ru($CH_3CN$)$_3$(triphos)]($CF_3SO_3$)$_2$ (840 mg) in 10 ml of methanol at room temperature, and the mixture was stirred for 15 minutes. Precipitated crystals were collected by suction filtration under an argon atmosphere, and were washed with 20 ml of cold methanol and 20 ml of diethyl ether.

[Ru(H)($BH_4$)(triphos)] 360 mg (yield 65%)

$^1$H NMR ($CD_2Cl_2$, −70 deg.): 7.50 br t (4H), 7.23 br t (4H), 7.10 m (6H), 6.23 m (16H), 5.15 br s (2H), 2.20 m (6H), 1.60 br (3H)

$^{31}$P[$^1$H] NMR ($CD_2Cl_2$) external reference $H_3PO_4$:58.1 d ($J_{pp}$=19 Hz, 2P), 14.83 t ($J_{pp}$=19 Hz, 1P)

Synthesis of [$Ru_2(\mu\text{-Cl})_3$(triphos-Tol)$_2$]Cl

Under an argon atmosphere, triphos-Tol (28.4 mg) dissolved by heating in 2 ml of toluene, was added dropwise to a suspension of [$RuCl_2(DMSO)_4$] (19.4 mg) in 1 ml of toluene at 80° C. The mixture was heated and stirred at the same temperature for one hour, and at 90° C. for 14 hours. The reaction liquid was left to cool to room temperature, and then precipitated crystals were collected by suction filtration under an argon atmosphere, and were washed with 1 ml of toluene and 1 ml of diethyl ether.

[$Ru_2(\mu\text{-Cl})_3$(triphos-Tol)$_2$]Cl 22.2 mg (yield 63%)

$^1$H NMR ($CD_2Cl_2$):7.30 br d (24H), 6.70 d (24H), 2.53 br s (12H), 2.27 s (24H), 1.54 br q (6H)

$^{31}$P[$^1$H] NMR ($CDCl_3$) external reference $H_3PO_4$:32.65 s

Synthesis of [$Ru_2(\mu\text{-Cl})_3$(tBu-triphos)$_2$]Cl

Under an argon atmosphere, tBu-triphos (66.6 mg) dissolved by heating in 4 ml of toluene, was added dropwise to a suspension of [$RuCl_2(DMSO)_4$] (48.4 mg) in 2 ml of toluene at 80° C. The mixture was heated and stirred at the same temperature for one hour, and at 90° C. for 14 hours. The reaction liquid was left to cool to room temperature, and then precipitated crystals were collected by suction filtration under an argon atmosphere, and were washed with 1 ml of toluene and 1 ml of diethyl ether.

[$Ru_2(\mu\text{-Cl})_3$(tBu-triphos)$_2$]Cl 42.3 mg (yield 50%)

$^1$H NMR ($CD_2Cl_2$):7.44 br t (24H), 7.21 t (12H), 6.93 t (24H), 2.39 br s (12H), 1.08 s (18H)

$^{31}$P[$^1$H] NMR ($CDC_2Cl_2$) external reference $H_3PO_4$:32.60 s

Example 1

Hydrogenation of methyl DL-mandelate

Methyl DL-mandelate (1.04 g), [$Ru_2(\mu\text{-Cl})_3$(triphos)$_2$]Cl (3.0 mg), potassium tert-butoxide (4.0 mg) and 2.5 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 1-phenyl-1,2-ethanediol was produced at a yield of 97.4%.

Example 2

Hydrogenation of methyl DL-lactate

[Ru$_2$(μ-Cl)$_3$(triphos)$_2$]Cl (4.0 mg), potassium tert-butoxide (5.5 mg), and 1.6 ml of methanol were added into a 20-ml Schlenk tube under an argon atmosphere, and the mixture was stirred for 5 minutes at room temperature. This solution, and methyl DL-lactate (0.85 g) dissolved in 2.0 ml of methanol were added to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 1,2-propanediol was produced at a yield of 99.9% or more.

Example 3

Hydrogenation of methyl DL-lactate

Methyl DL-lactate (3.21 g), [Ru$_2$(μ-Cl)$_3$(triphos)$_2$]Cl (3.0 mg), potassium tert-butoxide (5.5 mg) and 9.6 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 120° C. for 16 hours. After cooling, the reaction liquid was analyzed by gas chromatography, and it was found that 1,2-propanediol was produced at a yield of 88.5%.

Example 4

Hydrogenation of methyl DL-lactate

[Ru$_2$(μ-Cl)$_3$(triphos)$_2$]Cl (5.0 mg), lithium tert-butoxide (1.6 mg) and 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at an external temperature of 80° C. for 1 hour. After cooling, the autoclave was purged with hydrogen, and methyl DL-lactate (1.06 g) dissolved in 2.2 ml of methanol was added thereto under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 1,2-propanediol was produced at a yield of 99.9% or more.

Example 5

Hydrogenation of methyl DL-lactate

[Ru$_2$(μ-Cl)$_3$(triphos)$_2$]Cl (5.0 mg), sodium tetraphenylborate (14.0 mg), methyl DL-lactate (1.04 g), and 3.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 13 hours. After cooling, the reaction liquid was analyzed by gas chromatography, and it was found that 1,2-propanediol was produced at a yield of 73.5%.

Example 6

Hydrogenation of methyl DL-lactate

Methyl DL-lactate (0.64 g), [Ru$_2$(μ-Cl)$_3$(triphos)$_2$]Cl (3.0 mg), potassium tert-butoxide (5.5 mg), and 1.9 ml of methanol were added into a 100-ml autoclave having a stirrer placed inside, under an argon atmosphere. The autoclave was purged with hydrogen, and then hydrogen was further included in the autoclave up to 2.0 MPa. The contents of the autoclave were heated and stirred at 120° C. for 16 hours. After cooling, the reaction liquid was analyzed by gas chromatography, and it was found that 1,2-propanediol was produced at a yield of 67.1%.

Example 7

Hydrogenation of methyl DL-lactate

[Ru(CH$_3$CN)$_3$(triphos)] (CF$_3$SO$_3$)$_2$ (11.5 mg), methyl DL-lactate (2.10 g), and 6.2 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 14 hours. After cooling, the reaction liquid was analyzed by gas chromatography, and it was found that 1,2-propanediol was produced at a yield of 99.9% or more.

Example 8

Hydrogenation of methyl DL-lactate

[Ru(H)(BH$_4$)(triphos)] (7.4 mg), triethylamine (72.6 mg), methyl DL-lactate (2.10 g), and 6.2 ml of methanol were added into a 20-ml Schlenk tube under a nitrogen atmosphere, and the mixture was stirred for 5 minutes at room temperature. This solution was transferred to a 100-ml autoclave having a stirrer placed inside, under a nitrogen atmosphere. The autoclave was purged with hydrogen, and then hydrogen was further included in the autoclave up to 4.0 MPa. The contents of the autoclave were heated and stirred at 80° C. for 13 hours. After cooling, the reaction liquid was analyzed by gas chromatography, and it was found that 1,2-propanediol was produced at a yield of 98.2%.

Example 9

Hydrogenation of methyl hydroxyisobutyrate

[Ru$_2$(μ-Cl)$_3$(triphos)$_2$]Cl (8.2 mg), potassium tert-butoxide (18.4 mg), methyl hydroxyisobutyrate (0.48 g), and 1.9 ml of methanol were added into a 20-ml Schlenk tube under an argon atmosphere, and the mixture was stirred for 5 minutes at room temperature. This solution was transferred to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 13 hours. After cooling, the reaction liquid was analyzed by gas chromatography, and it was found that 2-methyl-1,2-propanediol was produced at a yield of 90.4%.

Example 10

Hydrogenation of γ-butyrolactone

[Ru$_2$(μ-Cl)$_3$(triphos)$_2$]Cl (3.0 mg), potassium tert-butoxide (5.5 mg), and 1.5 ml of methanol were added into a 20-ml Schlenk tube under a nitrogen atmosphere, and the mixture was stirred for 20 minutes at room temperature. This solution and γ-butyrolactone (0.11 g) were added into a 100-ml autoclave having a stirrer placed inside, under a nitrogen atmosphere. The autoclave was purged with hydrogen, and then hydrogen was further included in the autoclave up to 4.0 MPa. The contents of the autoclave were heated and stirred at 100° C. for 13 hours. After cooling, the reaction liquid was analyzed by gas chromatography, and it was found that 1,4-butanediol was produced at a yield of 69.0%.

Example 11

Hydrogenation of α-methyl-γ-butyrolactone

[Ru$_2$(μ-Cl)$_3$(triphos)$_2$]Cl (3.0 mg), potassium tert-butoxide (5.5 mg), and 1.5 ml of methanol were added into a 20-ml Schlenk tube under a nitrogen atmosphere, and the mixture was stirred for 20 minutes at room temperature. This solution and α-methyl-γ-butyrolactone (0.12 g) were added into a 100-ml autoclave having a stirrer placed inside, under a nitrogen atmosphere. The autoclave was purged with hydrogen, and then hydrogen was further included in the autoclave up to 4.0 MPa. The contents of the autoclave were heated and stirred at 100° C. for 13 hours. After cooling, the reaction liquid was analyzed by gas chromatography, and it was found that 1,4-pentanediol was produced at a yield of 39.7%.

Example 12

Hydrogenation of methyl benzoate

[Ru$_2$(μ-Cl)$_3$(triphos)$_2$]Cl (10.0 mg), potassium tert-butoxide (13.1 mg), and 2.6 ml of methanol were added into a 20-ml Schlenk tube under a nitrogen atmosphere, and the mixture was stirred for 10 minutes at room temperature. This solution and methyl benzoate (0.54 g) were added into a 100-ml autoclave having a stirrer placed inside, under a nitrogen atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that benzyl alcohol was produced at a yield of 54.1%.

Example 13

Hydrogenation of methyl 3-phenylpropionate

[Ru$_2$(μ-Cl)$_3$(triphos)$_2$]Cl (10.0 mg), lithium tert-butoxide (13.1 mg), and 1.6 ml of methanol were added into a 20-ml Schlenk tube under an argon atmosphere, and the mixture was stirred for 30 minutes at room temperature. This solution, and methyl 3-phenylpropionate (0.65 g) dissolved in 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 14 hours. After cooling, the reaction liquid was analyzed by gas chromatography, and it was found that 3-phenyl-1-propanol was produced at a yield of 68.2%.

Example 14

Hydrogenation of methyl 3-phenylpropionate

[Ru$_2$(μ-Cl)$_3$(triphos)$_2$]Cl (10.0 mg), 10% lithium methoxide (60.8 mg), and 1.0 ml of methanol were added into a 20-ml Schlenk tube under an argon atmosphere, and the mixture was stirred for one hour at room temperature. This solution, and methyl 3-phenylpropionate (0.66 g) dissolved in 1.6 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 3-phenyl-1-propanol was produced at a yield of 62.1%.

Example 15

Hydrogenation of methyl 3-phenylpropionate

[Ru$_2$(μ-Cl)$_3$(triphos)$_2$]Cl (10.0 mg), 30% potassium methoxide (37.4 mg), and 1.0 ml of methanol were added into a 20-ml Schlenk tube under an argon atmosphere, and the mixture was stirred for one hour at room temperature. This solution, and methyl 3-phenylpropionate (0.66 g) dissolved in 1.6 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 3-phenyl-1-propanol was produced at a yield of 59.4%.

Example 16

Hydrogenation of methyl 3-phenylpropionate

[Ru(H)(BH$_4$)(triphos)] (7.4 mg), lithium tert-butoxide (24.0 mg), and 1.6 ml of methanol were added into a 20-ml Schlenk tube under an argon atmosphere, and the mixture was stirred for one hour at room temperature. This solution, and methyl 3-phenylpropionate (0.66 g) dissolved in 1.6 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 3-phenyl-1-propanol was produced at a yield of 34.4%.

Example 17

Hydrogenation of methyl 3-phenylpropionate

[Ru(H)(BH$_4$)(triphos)] (14.8 mg), triethylamine (36.3 mg), and 2.0 ml of methanol were added into a 20-ml Schlenk tube under an argon atmosphere, and the mixture was stirred for one hour at room temperature. This solution, and methyl 3-phenylpropionate (1.31 g) dissolved in 3.2 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed, and it was found that 3-phenyl-1-propanol was produced at a yield of 17.4%.

Example 18

Hydrogenation of ethyl 3-phenylpropionate

[Ru$_2$(μ-Cl)$_3$(triphos)$_2$]Cl (10.0 mg), a 10% methanol solution of lithium methoxide (60.8 mg), and 1.6 ml of methanol were added into a 20-ml Schlenk tube under an argon atmosphere, and the mixture was stirred for 10 minutes at room temperature. This solution, and ethyl 3-phenylpropionate (0.71 g) dissolved in 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 3-phenyl-1-propanol was produced at a yield of 20.5%.

Example 19

Hydrogenation of methyl cinnamate

[Ru$_2$(μ-Cl)$_3$(triphos)$_2$]Cl (10.0 mg), a 10% methanol solution of lithium methoxide (60.8 mg), and 1.6 ml of methanol were added into a 20-ml Schlenk tube under an argon atmosphere, and the mixture was stirred for 10 minutes at room temperature. This solution, and methyl cinnamate (0.65 g) dissolved in 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 15 hours. After cooling, the reaction liquid was analyzed by gas chromatography, and it was found that 3-phenyl-1-propanol was produced at a yield of 27.5%.

Example 20

Hydrogenation of phenylalanine methyl ester

[Ru$_2$(μ-Cl)$_3$(triphos)$_2$]Cl (3.0 mg), potassium tert-butoxide (5.5 mg), and 2.0 ml of methanol were added into a 20-ml Schlenk tube under an argon atmosphere, and the mixture was stirred for 30 minutes at room temperature. This solution, and phenylalanine methyl ester (0.22 g) suspended in 2.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 16 hours. After cooling, the reaction liquid was analyzed by high performance liquid chromatography, and it was found that phenylalaminol was produced at a yield of 7.4%.

Example 21

Hydrogenation of N-Boc-phenylalanine methyl ester

[Ru$_2$(μ-Cl)$_3$(triphos)$_2$]Cl (3.0 mg), potassium tert-butoxide (5.5 mg), and 2.0 ml of methanol were added into a 20-ml Schlenk tube under an argon atmosphere, and the mixture was stirred for 30 minutes at room temperature. This solution, and N-Boc-phenylalanine methyl ester (0.34 g) suspended in 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 16 hours. After cooling, the reaction liquid was analyzed by high performance liquid chromatography, and it was found that N-Boc-phenylalaminol was produced at a yield of 19.3%.

Example 22

Hydrogenation of N-benzoyl-phenylalanine methyl ester

[Ru$_2$(μ-Cl)$_3$(triphos)$_2$]Cl (3.0 mg), potassium tert-butoxide (5.5 mg), and 2.0 ml of methanol were added into a 20-ml Schlenk tube under an argon atmosphere, and the mixture was stirred for 30 minutes at room temperature. This solution, and N-benzoyl-phenylalanine methyl ester (0.35 g) suspended in 1.0 ml of methanol were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 16 hours. After cooling, the reaction liquid was analyzed by high performance liquid chromatography, and it was found that N-benzoylphenylalaminol was produced at a yield of 37.7%.

Example 23

Hydrogenation of methyl 3-hydroxybutanoate

[Ru(CH$_3$CN)$_3$(triphos)](CF$_3$SO$_3$)$_2$ (11.5 mg), methyl 3-hydroxybutanoate (0.47 g), and 1.5 ml of methanol were added into a 20-ml Schlenk tube under an argon atmosphere, and the mixture was stirred for 5 minutes at room temperature. This solution was transferred to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 120° C. for 13 hours. After cooling, the reaction liquid was analyzed by gas chromatography, and it was found that 1,3-butanediol was produced at a yield of 44.5%.

Example 24

Hydrogenation of dimethyl DL-malate

[Ru(CH$_3$CN)$_3$(triphos)](CF$_3$SO$_3$)$_2$ (11.5 mg), dimethyl DL-malate (0.16 g), and 1.0 ml of methanol were added into a 20-ml Schlenk tube under an argon atmosphere, and the mixture was stirred for 5 minutes at room temperature. This solution was transferred to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 14 hours. After cooling, the reaction liquid was analyzed by gas chromatography, and it was found that 1,2,4-butanetriol was produced at a yield of 99.9% or more.

Example 25

Hydrogenation of dimethyl DL-malate

[Ru(H)(BH$_4$)(triphos)] (7.4 mg), dimethyl DL-malate (0.16 g), and 1.0 ml of methanol were added into a 20-ml Schlenk tube under an argon atmosphere, and the mixture was stirred for 5 minutes at room temperature. This liquid was transferred to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 14 hours. After cooling, the reaction liquid was analyzed by gas chromatography, and it was found that 1,2,4-butanetriol was produced at a yield of 99.9% or more.

Example 26

Hydrogenation of dimethyl DL-malate

[Ru(CH$_3$CN)$_3$(triphos)](CF$_3$SO$_3$)$_2$ (11.5 mg), dimethyl DL-malate (0.65 g), and 1.0 ml of methanol were added into a 20-ml Schlenk tube under an argon atmosphere, and the mixture was stirred for 5 minutes at room temperature. This liquid was transferred to a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 100° C. for 14 hours. After cooling, the reaction liquid was analyzed by gas chromatography, and it was found that 1,2,4-butanetriol was produced at a yield of 30.6%, β-hydroxy-γ-butyrolactone at a yield of 42.3%, and methyl 3,4-dihydroxybutanoate at a yield of 21.4%.

Example 27

Hydrogenation of methyl D-(+)-lactate

[Ru$_2$(μ-Cl)$_3$(triphos)$_2$]Cl (8.4 mg), potassium tert-butoxide (18.6 mg), and methyl D-(+)-lactate (optical purity: 99.2% ee) (0.85 g) were added into a 100-ml autoclave equipped with a glass inner tube, and the autoclave was purged with hydrogen. 3.0 ml of methanol was added thereto under an argon atmosphere, the autoclave was purged with hydrogen, and then hydrogen was further included in the autoclave up to 4.0 MPa. The contents of the autoclave were heated and stirred at 100° C. for 12 hours. After cooling, the reaction liquid was analyzed by gas chromatography, and it was found that (2R)-1,2-propanediol was produced at a yield of 99.9% or more. The product was further induced to a bis-benzoate form and was analyzed, and as a result, the optical purity was found to be 93.6% ee.

Example 28

Hydrogenation of methyl D-(+)-lactate

[Ru(H)(BH$_4$)(triphos)] (7.4 mg), lithium tert-butoxide (2.4 mg), and 3.1 ml of methanol were added into a 20-ml Schlenk tube under an argon atmosphere, and the mixture was stirred for 5 minutes at room temperature. This liquid and methyl D-(+)-lactate (optical purity: 99.2% ee) (1.04 g) were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 70° C. for 14 hours. After cooling, the reaction liquid was analyzed by gas chromatography, and it was found that (2R)-1,2-propanediol was produced at a yield of 97.1%. The product was further induced to a bis-benzoate form and was analyzed, and as a result, the optical purity was found to be 91.5% ee.

Example 29

Hydrogenation of methyl D-(+)-lactate

[Ru(H)(BH$_4$)(triphos)] (7.4 mg), lithium tert-butoxide (8.0 mg), and 3.1 ml of methanol were added into a 20-ml Schlenk tube under an argon atmosphere, and the mixture was stirred for 5 minutes at room temperature. This liquid and methyl D-(+)-lactate (optical purity: 99.2% ee) (1.04 g) were added into a 100-ml autoclave having a stirrer placed inside, under an argon atmosphere. The autoclave was purged with hydrogen, and then hydrogen was further included in the autoclave up to 4.0 MPa. The contents of the autoclave were heated and stirred at 70° C. for 14 hours. After cooling, the reaction liquid was analyzed by gas chromatography, and it was found that (2R)-1,2-propanediol was produced at a yield of 73.8%. The product was further induced to a bis-benzoate form and was analyzed, and as a result, the optical purity was found to be 93.5% ee.

Example 30

Hydrogenation of methyl DL-mandelate

Methyl DL-mandelate (332.3 mg), [RuCl$_2$(p-cymene)]$_2$ (3.1 mg), 1,1,1-tris(diphenylphosphinomethyl)ethane (6.2 mg), potassium tert-butoxide (10.6 mg) and 3 ml of methanol were added into a 100-ml autoclave having a stirrer placed inside, under an argon atmosphere. The autoclave was purged with hydrogen, and then hydrogen was further included in the autoclave up to 3.0 MPa. The contents of the autoclave were heated and stirred at 110° C. for 14 hours. After cooling, the reaction liquid was analyzed by gas chromatography, and it was found that 1-phenyl-1,2-ethanediol was produced at a yield of 99.9% or more.

Example 31

Hydrogenation of methyl DL-mandelate

Methyl DL-mandelate (332.3 mg), [Ru(cod)Cl$_2$] (2.8 mg), 1,1,1-tris(diphenylphosphinomethyl)ethane (6.2 mg), potassium tert-butoxide (10.6 mg) and 3 ml of methanol were added into a 100-ml autoclave having a stirrer placed inside, under an argon atmosphere. The autoclave was purged with hydrogen, and then hydrogen was further included in the autoclave up to 3.0 MPa. The contents of the autoclave were heated and stirred at 110° C. for 14 hours. After cooling, the reaction liquid was analyzed by gas chromatography, and it was found that 1-phenyl-1,2-ethanediol was produced at a yield of 99.9% or more.

Example 32

Hydrogenation of methyl DL-mandelate

Methyl DL-mandelate (332.3 mg), [RuCl$_2$(benzene)]$_2$ (2.5 mg), 1,1,1-tris(diphenylphosphinomethyl)ethane (6.2 mg), potassium tert-butoxide (10.6 mg) and 3 ml of methanol were added into a 100-ml autoclave having a stirrer placed inside, under an argon atmosphere. The autoclave was purged with hydrogen, and then hydrogen was further included in the autoclave up to 3.0 MPa. The contents of the autoclave were heated and stirred at 110° C. for 14 hours. After cooling, the reaction liquid was analyzed by gas chromatography, and it was found that 1-phenyl-1,2-ethanediol was produced at a yield of 26.5%.

Example 33

Hydrogenation of methyl DL-lactate

Methyl DL-lactate (1.04 g), [Ru$_2$(μ-Cl)$_3$(triphos-Tol)$_2$]Cl (8.8 mg), potassium tert-butoxide (17.9 mg), and 3.0 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 98.4%.

Example 34

Hydrogenation of methyl DL-lactate

Methyl DL-lactate (1.04 g), [Ru$_2$(μ-Cl)$_3$(tBu-triphos)$_2$]Cl (8.4 mg), potassium tert-butoxide (17.9 mg), and 3.0 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 90.6%.

Example 35

Hydrogenation of methyl DL-lactate

Methyl DL-lactate (1.04 g), [Ru(H)(OAc)(triphos)] (7.9 mg), and 3.0 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 99.9% or more.

Example 36

Hydrogenation of methyl DL-lactate

Methyl DL-lactate (1.04 g), [Ru(H)(OAc)(triphos)] (7.9 mg), potassium tert-butoxide (9.8 mg), and 3.0 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 99.9% or more.

Example 37

Hydrogenation of methyl DL-lactate

Methyl DL-lactate (1.04 g), [Ru(H)(OAc)(triphos)] (7.9 mg), acetic acid (10.0 mg), and 3.0 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 63.5%.

Example 38

Hydrogenation of methyl DL-lactate

Methyl DL-lactate (1.04 g), [RuCl$_2$(benzene)]$_2$ (5.0 mg), triphos (6.2 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 16 hours. After cooling, the reaction liquid was analyzed by gas chromatography, and it was found that 1,2-propanediol was produced at a yield of 95.0%.

Example 39

Hydrogenation of methyl DL-lactate

Methyl DL-lactate (1.04 g), RuCl$_2$(PPh$_3$)$_3$ (9.6 mg), triphos (6.2 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 16 hours. After cooling, the reaction liquid was analyzed by gas chromatography, and it was found that 1,2-propanediol was produced at a yield of 44.8%.

Example 40

Hydrogenation of methyl DL-lactate

Methyl DL-lactate (1.04 g), RuH$_2$(PPh$_3$)$_4$ (11.5 mg), triphos (6.2 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 16 hours. After cooling, the reaction liquid was analyzed by gas chromatography, and it was found that 1,2-propanediol was produced at a yield of 99.9% or more.

Example 41

Hydrogenation of methyl DL-lactate

Methyl DL-lactate (1.04 g), RuH$_2$(PPh$_3$)$_4$ (11.5 mg), tBu-triphos (6.7 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 99.9% or more.

Example 42

Hydrogenation of methyl DL-lactate

Methyl DL-lactate (1.04 g), RuH$_2$(PPh$_3$)$_4$ (11.5 mg), H-triphos (6.7 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 15 hours. After cooling, the reaction liquid was analyzed by gas chromatography, and it was found that 1,2-propanediol was produced at a yield of 32.8%.

Example 43

Hydrogenation of methyl D-(+)-lactate

Methyl D-(+)-lactate (optical purity: 99.2% ee) (0.52 g), RuH$_2$(PPh$_3$)$_4$ (11.5 mg), triphos (6.2 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 80° C. for 13 hours. After cooling, the reaction liquid was analyzed by gas chromatography, and it was found that (2R)-1,2-propanediol was produced at a yield of 82.5%. The product was further induced to a carbonate form and was analyzed, and as a result, the optical purity was found to be 88.9% ee.

Example 44

Hydrogenation of methyl D-(+)-lactate

Methyl D-(+)-lactate (optical purity: 99.2% ee) (1.04 g), RuH$_2$(PPh$_3$)$_4$ (11.5 mg), triphos (6.2 mg), sodium methoxide (2.7 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 80° C. for 13 hours. After cooling, the reaction liquid was analyzed by gas chromatography, and it was found that (2R)-1,2-propanediol was produced at a yield of 91.8%. The product was further induced to a carbonate form and was analyzed, and as a result, the optical purity was found to be 94.0% ee.

Example 45

Hydrogenation of methyl D-(+)-lactate

Methyl D-(+)-lactate (optical purity: 99.2% ee) (0.64 g), [RuH$_2$(PPh$_3$)$_4$] (2.8 mg), triphos-An.3BH$_3$ (8.5 mg), sodium methoxide (5.4 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 80° C. for 13 hours. After cooling, the reaction liquid was analyzed by gas chromatography, and it was found that (2R)-1,2-propanediol was produced at a yield of 63.9%. The product was further induced to a carbonate form and was analyzed, and as a result, the optical purity was found to be 92.8% ee.

Reference Experiment 1

The results of performing the hydrogenation of methyl DL-lactate without using the tridentate ligand used in the present invention, are presented below.

Methyl DL-lactate (1.04 g), RuH$_2$(PPh$_3$)$_4$ (11.5 mg), and 3 ml of methanol were added into a 100-ml autoclave having a stirrer placed inside, under a nitrogen atmosphere. The autoclave was purged with hydrogen, and then hydrogen was further included in the autoclave up to 5.0 MPa. The contents of the autoclave were heated and stirred at 100° C. for 16 hours. After cooling, the reaction liquid was analyzed by gas chromatography, and it was found that 1,2-propanediol was produced in a trace amount.

As shown by the results above, when a tridentate ligand was not used, the reaction did not proceed.

The invention claimed is:
1. A method for producing an alcohol, comprising subjecting a lactone or a carboxylic acid ester to hydrogen reduction in a solvent or without solvent, in the presence of a catalyst containing ruthenium and a phosphine compound represented by the following formula (1):

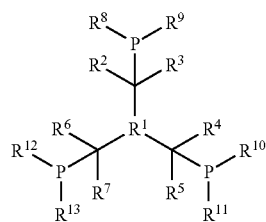

(1)

wherein R$^1$ represents a spacer; R$^2$, R$^3$, R$^4$, R$^5$, R$^6$ and R$^7$ each independently represent a hydrogen atom, or an alkyl group having 1 to 12 carbon atoms, an aryl group or a heterocyclic group; and R$^8$, R$^9$, R$^{10}$, R$^{11}$, R$^{12}$ and R$^{13}$ each independently represent an alkyl group having 1 to 12 carbon atoms, an aryl group or a heterocyclic group.

2. The method for production according to claim 1, wherein the lactone or carboxylic acid ester that is subjected to reduction is an optically active form, and the optical purity of the alcohol produced by the reduction retains an optical purity value of 90% or more of the value of the substrate that is subjected to reduction.

3. The method for production according to claim 1, wherein the catalyst containing ruthenium and a phosphine compound is produced for immediate use.

4. The method for production according to claim 1, wherein the catalyst containing ruthenium and a phosphine compound is a complex represented by the following formula (2):

$$[Ru_2(\mu-X^1)_3(Phos)_2]X^2 \qquad (2)$$

wherein X$^1$ represents a halogen atom; X$^2$ represents a counter anion; and Phos represents the phosphine compound represented by the formula (1).

5. The method for production according to claim 1, wherein the catalyst containing ruthenium and a phosphine compound is a complex represented by the following formula (3):

$$[Ru(Phos)(L^1)(L^2)(L^3)](X^3)_2 \qquad (3)$$

wherein $L^1$, $L^2$ and $L^3$, which may be present singly or linked together, each represent a neutral ligand or a coordinating solvent; $X^3$ represents a counter anion; and Phos represents the phosphine compound represented by the formula (1).

6. The method for production according to claim 1, wherein the catalyst containing ruthenium and a phosphine compound is a complex represented by the following formula (4):

$$[RuH(BH_4)(Phos)] \qquad (4)$$

wherein Phos represents the phosphine compound represented by the formula (1).

7. The method for production according to claim 1, wherein the catalyst containing ruthenium and a phosphine compound is a complex represented by the following formula (5):

$$[Ru(H)(OAc)(Phos)] \qquad (5)$$

wherein Ac represents an acetyl group; and Phos represents the phosphine compound represented by the formula (1).

8. The method for production according to claim 1, wherein the solvent used in the hydrogenation reaction is an alcohol solvent.

9. The method for production according to claim 1, wherein an additive is added to the reaction system.

10. The method for production according to claim 1, wherein a reducing agent is added to the reaction system as a co-catalyst.

* * * * *